(12) United States Patent
Garcia Molina (10) Patent No.: US 10,548,524 B2
(45) Date of Patent: Feb. 4, 2020

(54) SYSTEM AND METHOD FOR DETERMINING SLEEP NEED DISSIPATION WITHOUT MONITORING BRAIN ACTIVITY DURING A SLEEP SESSION

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/306,020

(22) PCT Filed: Jun. 2, 2017

(86) PCT No.: PCT/EP2017/063409
§ 371 (c)(1),
(2) Date: Nov. 30, 2018

(87) PCT Pub. No.: WO2017/215948
PCT Pub. Date: Dec. 21, 2017

(65) Prior Publication Data
US 2019/0142335 A1    May 16, 2019

Related U.S. Application Data

(60) Provisional application No. 62/351,587, filed on Jun. 17, 2016.

(51) Int. Cl.
*H04N 19/14* (2014.01)
*A61B 5/00* (2006.01)
(Continued)

(52) U.S. Cl.
CPC ........ *A61B 5/4806* (2013.01); *A61B 5/04842* (2013.01); *A61B 5/7235* (2013.01);
(Continued)

(58) Field of Classification Search
USPC ......................................................... 340/575
See application file for complete search history.

(56) References Cited

U.S. PATENT DOCUMENTS

| | | |
|---|---|---|
| 9,149,599 B2 * | 10/2015 | Walter ................. A61M 21/02 |
| 10,232,139 B1 * | 3/2019 | Hang .................... A61M 21/02 |
| 2018/0078734 A1 * | 3/2018 | Pfundtner ............ A61B 5/4812 |

OTHER PUBLICATIONS

Cao, T. et al., "Objective evaluation of fatigue by EEG spectral analysis in steady-state visual evoked potential-based brain-computer interfaces", BioMedical Engineering Online, 2014.
(Continued)

*Primary Examiner* — Brent Swarthout (57) ABSTRACT

A system configured to determine sleep need dissipation without monitoring brain activity during a sleep session. The system comprises a sensory stimulator configured to provide repetitive visual stimulation (RVS); a sensor configured to generate output signals conveying information related to brain activity; and one or more hardware processors configured to: before the sleep session, cause the one or more sensory stimulators to provide first RVS, and determine a first steady state visually evoked potential (SSVEP) response based on the output signals during the first RVS; and after the sleep session, cause the one or more sensory stimulators to provide second RVS, determine a second SSVEP response based on the output signals during the second RVS; compare the second SSVEP response to the first SSVEP response, and determine the sleep need dissipation for the sleep session based on the comparison.

15 Claims, 6 Drawing Sheets

(51) Int. Cl.
*A61B 5/0484* (2006.01)
*A61M 21/02* (2006.01)
*A61M 21/00* (2006.01)

(52) U.S. Cl.
CPC ..... *A61M 21/02* (2013.01); *A61M 2021/0044* (2013.01); *A61M 2021/0083* (2013.01)

(56) References Cited

OTHER PUBLICATIONS

B. K. Hulse, E. C. Landsness, S. Sarasso, F. Ferrarelli, J. J. Guokas, T. Wanger, and G. Tononi, "A postsleep decline in auditory evoked potential amplitude reflects sleep homeostasis.," Clin. Neurophysiol., vol. 122, No. 8, pp. 1549-1555, Aug. 2011.

G. Tononi and C. Cirelli, "Sleep function and synaptic homeostasis.," Sleep Med. Rev., vol. 10, No. 1, pp. 49-62, Feb. 2006.

B. A. Riedner, B. K Hulse, F. Ferrarelli, S. Sarasso, and G. Tononi, "Enhancing sleep slow waves with natural stimuli," Medicamundi, vol. 45, No. 2, pp. 82-88, 2010.

P. Achermann and A. A. Borbely, "Mathematical models of sleep regulation.," Front. Biosci. a J. virtual Libr., vol. 8, No. 13, pp. s683-s693, 2003.

A. A. Borbély and P. Achermann, "Sleep Homeostasis and Models of Sleep Regulation," J. Biol. Rhythms, vol. 14, No. 6, pp. 559-570, Dec. 1999.

T. L. Huang and C. Charyton, "A comprehensive review of the psychological effects of brainwave entrainment," Altern. Ther., vol. 14, No. 5, pp. 38-50, 2008.

M. A. Pastor, J. Artieda, J. Arbizu, M. Valencia, and J. C. Masdeu, "Human Cerebral Activation during Steady-State Visual-Evoked Responses," J. Neurosci., vol. 23, No. 37, pp. 11621-11627, 2003.

\* cited by examiner

SYSTEM AND METHOD FOR DETERMINING SLEEP NEED DISSIPATION WITHOUT MONITORING BRAIN ACTIVITY DURING A SLEEP SESSION

CROSS-REFERENCE TO PRIOR APPLICATIONS

This application is the U.S. National Phase application under 35 U.S.C. § 371 of International Application Serial No. PCT/EP2017/063409, filed on 2 Jun. 2017, which claims the benefit of U.S. Provisional Application No. 62/351,587, filed on 17 Jun. 2016. These applications are hereby incorporated by reference herein.

BACKGROUND

1. Field

The present disclosure pertains to a system configured to determine sleep need dissipation in a subject without monitoring brain activity during a sleep session.

2. Description of the Related Art

Systems for monitoring sleep are known. Typical sleep monitoring systems require a subject to wear auditory stimulation equipment and electroencephalogram (EEG) electrodes throughout a sleep session. These devices may disrupt the sleep of the subject. The present disclosure overcomes deficiencies in prior art systems.

SUMMARY

Accordingly, one or more aspects of the present disclosure relate to a system configured to determine sleep need dissipation in a subject without monitoring brain activity during a sleep session. The system comprises one or more sensory stimulators, one or more sensors, one or more hardware processors, and/or other components. The one or more sensory stimulators are configured to provide repetitive visual stimulation (RVS) to the subject. The one or more sensors are configured to generate output signals conveying information related to brain activity in the subject. The one or more hardware processors operatively communicate with the one or more sensory stimulators and the one or more sensors. The one or more hardware processors are configured by machine-readable instructions to: before the sleep session, (i) cause the one or more sensory stimulators to provide first RVS, and (ii) determine a first steady state visually evoked potential (SSVEP) response of the subject based on the output signals during the first RVS; and after the sleep session, (iii) cause the one or more sensory stimulators to provide second RVS, (iv) determine a second SSVEP response of the subject based on the output signals during the second RVS; (v) compare the second SSVEP response to the first SSVEP response, and (vi) determine the sleep need dissipation for the sleep session based on the comparison.

Yet another aspect of the present disclosure relates to a method for determining sleep need dissipation in a subject without monitoring brain activity during a sleep session. The method is performed by a determination system comprising one or more sensory stimulators, one or more sensors, one or more hardware processors, and/or other components. The method comprises, before the sleep session, with the one or more hardware processors, (i) causing the one or more sensory stimulators to provide first repetitive visual stimulation RVS, and (ii) determining a first steady state visually evoked potential (SSVEP) response of the subject based on output signals conveying information related to brain activity in the subject from the one or more sensors during the first RVS; and, after the sleep session, with the one or more hardware processors, (iii) causing the one or more sensory stimulators to provide second RVS, (iv) determining a second SSVEP response of the subject based on the output signals during the second RVS; (v) comparing the second SSVEP response to the first SSVEP response, and (vi) determining the sleep need dissipation for the sleep session based on the comparison.

Still another aspect of present disclosure relates to a system configured to determine sleep need dissipation in a subject without monitoring brain activity during a sleep session. The system comprises: means for providing repetitive visual stimulation (RVS) to the subject; means for generating output signals conveying information related to brain activity in the subject; and before the sleep session, means for (i) causing the means for providing to provide first RVS, and (ii) determining a first steady state visually evoked potential (SSVEP) response of the subject based on the output signals during the first RVS; and after the sleep session, means for (iii) causing the one or more sensory stimulators to provide second RVS, (iv) determining a second SSVEP response of the subject based on the output signals during the second RVS; (v) comparing the second SSVEP response to the first SSVEP response, and (vi) determining the sleep need dissipation for the sleep session based on the comparison.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
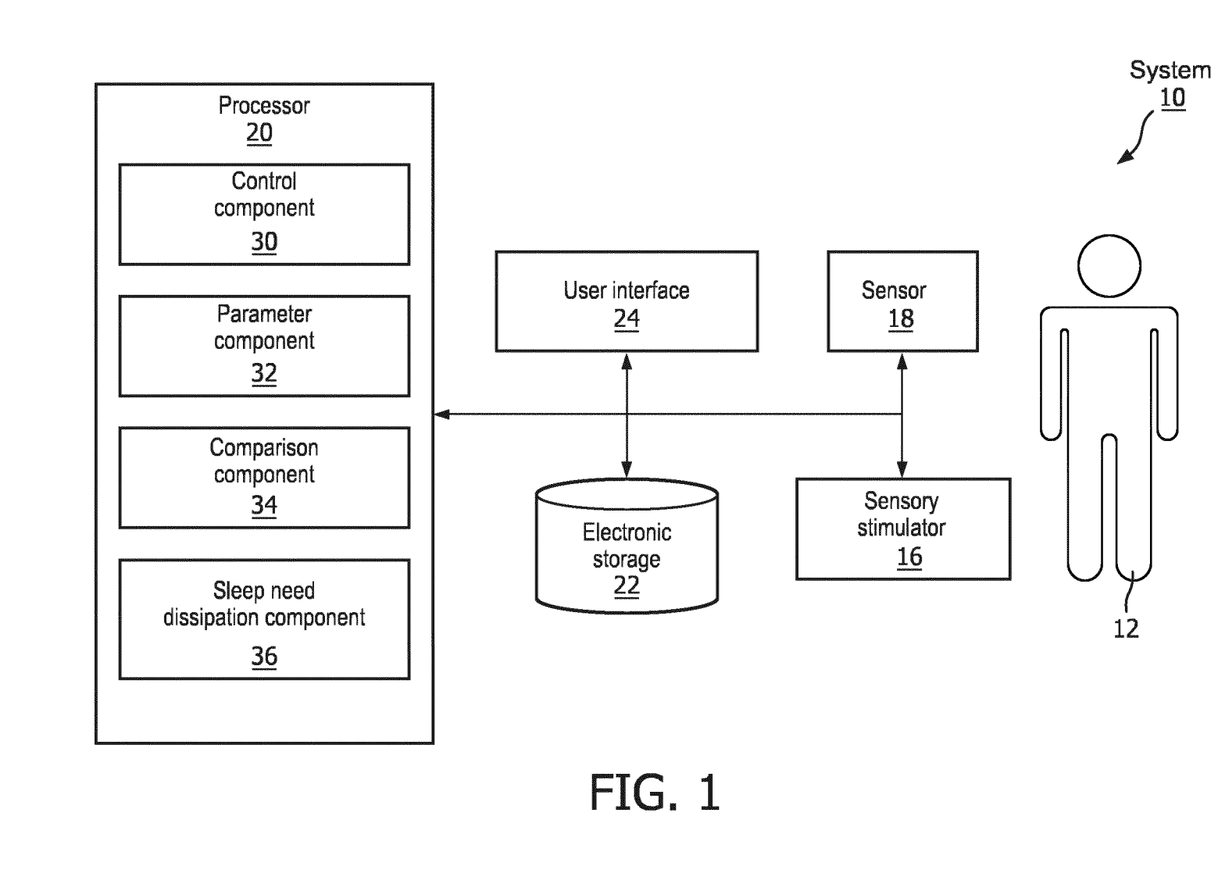
FIG. 1 illustrates a system configured to determine sleep need dissipation in a subject without monitoring brain activity during a sleep session.

FIG. 1 is a schematic illustration of a system 10 configured to determine sleep need dissipation in a subject 12 without monitoring brain activity during a sleep session. Sleep homeostasis and synaptic plasticity in subject 12 are related. During NREM sleep (due to the bi-stable state of the brain cortex which manifests as slow-waves identifiable via an electroencephalogram (EEG)) many synapses that were created during wakefulness are reduced and/or eliminated. Because of this reduction and/or elimination of synapses, the cortical synaptic strength of subject 12 decreases after a sleep session. The longer the duration of the sleep session, the weaker the cortical synaptic strength becomes. Slow wave activity (SWA) is a measure of sleep homeostasis that increases after waking and decreases after sleep. An integral of SWA up to a time "t" during a sleep session reflects the amount of sleep need dissipation up to time "t" for a subject during the sleep session.

Quantifying SWA requires the EEG to be recorded throughout an entire sleep session. This necessitates wearing an EEG acquisition system during the sleep session. There is a market need for a system configured to quantify sleep need dissipation (e.g., sleep restoration) without requiring the recording of an EEG (and/or the wearing of an EEG acquisition system) throughout an entire sleep session. Such a system might be used, for example, in applications such as coaching to promote appropriate sleep hygiene and/or monitoring of sleep medication effectiveness, non-EEG based alternatives that use cardio-respiratory and/or other signals to deliver stimulation, and/or other applications where it would be convenient to quantify sleep need dissipation without necessarily recording an EEG over the whole sleep session. Furthermore, even if an EEG is generated throughout an entire sleep session, subject specific (e.g. sweat) and/or external (e.g. electromagnetic noise, system failure and/or electrode detachment) artifacts may be present in the EEG signal that hinder the calculation of SWA values. In these instances, determining sleep need dissipation based on measurements made before and after the sleep session would be useful.

Cortical synaptic strength may be quantified during wakefulness by measuring the EEG response to auditory stimulation. The amplitude of the auditory evoked potential (AEP) decreases after a night of sleep. The extent of the amplitude decline correlates with the EEG power during NREM sleep in the frequency band from about 1 to about 2.33 Hz which, by virtue of being within the SWA range (0.5 to 4 Hz) of the frequency band, is a homeostatically regulated measure of sleep need (and/or sleep debt).

Instead of using an AEP caused by auditory stimulation, system 10 uses evoked responses to repetitive visual stimulation (RVS, e.g., flickering light and/or other RVS) which are known as steady state visual evoked potentials (SSVEP) to determine sleep need dissipation in a subject 12 without monitoring brain activity during a sleep session. SSVEP have a higher signal-to-noise ratio (SNR) as compared to auditory evoked potentials because visual stimulation is likely to engage a larger number of brain cortical areas as compared to auditory stimulation. This is because the amplitude of the EEG response is higher for the repetitive visual stimulation compared to auditory stimulation. In addition, given the repetitive nature of the stimulation, the time period during which the amplitude of the EEG signal remains at a high level for RVS is longer as compared to the time period during which the amplitude of the EEG signal remains at a high level for an evoked auditory response. Furthermore, the higher SNR property of visually evoked potentials facilitates shorter exposure to the repetitive visual stimulation relative to auditory stimulation that is required when determining sleep need dissipation in a subject 12 without monitoring brain activity during a sleep session.

In some embodiments, system 10 comprises one or more of a sensory stimulator 16, a sensor 18, a processor 20, electronic storage 22, a user interface 24, and/or other components. In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, some and/or all of the components of system 10 may be grouped as part of a headband and/or other garments worn by subject 12 before and/or after the sleep session, but removed during the sleep session.

Sensory stimulator 16 is configured to provide RVS and/or other sensory stimuli to subject 12. Sensory stimulator 16 is configured to provide the RVS and/or other sensory stimulation to subject 12 prior to a sleep session, after a sleep session, and/or at other times. For example, sensory stimulator 16 may be configured to provide RVS to subject 12 before subject 12 falls asleep and after subject 12 wakes from a sleep session. Sensory stimulator 16 may be configured to provide RVS to subject 12 to evoke brain activity responses to the RVS in subject 12. In some embodiments, the evoked responses may be and/or include the SSVEP and/or other responses. In some embodiments, sensory stimulator 16 may be configured to induce SSVEP responses through RVS and/or other non-invasive brain stimulation methods. Examples of sensory stimulator 16 may include one or more of a display screen of a computing device (e.g., a smartphone, a tablet computer, a laptop computer, a desktop computer, etc.), a lighting panel (e.g., an external panel similar to and/or the same as the Philips GoLite BLU), light emitting diodes (LED's), pattern reversal stimulators, and/or other devices. In some embodiments, sensory stimulator 16 may be included in a computing device that forms user interface 24 and/or other components of system 10. In some embodiments, sensory stimulator 16 may display a checkerboard pattern that alternates in color at a fixed constant frequency (e.g., 10-30 Hz and/or other frequencies).

Sensor 18 is configured to generate output signals conveying information related to brain activity of subject 12 and/or other information. Sensor 18 is configured to generate output signals in an ongoing manner before and/or after the sleep session of subject 12, at regular intervals before and/or after the sleep session, and/or at other times. The brain activity of subject 12 may correspond to the SSVEP responses, and/or other characteristics of subject 12. Sensor 18 may comprise one or more sensors that measure such parameters directly and/or indirectly. Although sensor 18 is illustrated at a single location near subject 12, this is not intended to be limiting. Sensor 18 may include sensors disposed in a plurality of locations, such as for example, coupled in a removable manner with the skin of subject 12, coupled in a removable manner with clothing of subject 12, worn by subject 12 (e.g., as a headband, wristband, etc.), within (or in communication with) sensory stimulator 16, and/or in other locations.

By way of a non-limiting example, sensor 18 may be and/or include one or more electrodes configured to detect electrical activity along the scalp of subject 12 resulting from current flows within the brain of subject 12. In some embodiments, sensor 18 is and/or includes a plurality of EEG electrodes, and/or other sensors. In some embodiments, the EEG electrodes are configured to be coupled at occipital locations on the head of subject 12. In some embodiments, the EEG electrodes are configured to be coupled at frontal locations on the head of subject 12. In these embodiments, the EEG electrodes (sensor 18) are coupled with the head of subject 12 before the sleep session, decoupled from subject 12 during (and/or shortly before) the sleep session, and recoupled with the head of subject 12 after the sleep session.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, sensor 18), or processor 20 may represent processing functionality of a plurality of devices operating in coordination.

As shown in FIG. 1, processor 20 is configured to execute one or more computer program components. The one or more computer program components may comprise one or more of a control component 30, a parameter component 32, a comparison component 34, a sleep need dissipation component 36, and/or other components. Processor 20 may be configured to execute components 30, 32, 34, 36, and/or other components by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, 36, and/or other components may be located remotely from the other components. The description of the functionality provided by the different components 30, 32, 34, 36, and/or other components described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Control component 30 is configured to control sensory stimulator 16 to provide RVS to subject 12 before and after a sleep session. For example, control component 34 is configured to control sensory stimulator 16 to provide first RVS to subject 12 before the sleep session and second RVS after the sleep session. In some embodiments, the first RVS is delivered within about 30 minutes of a start of the sleep session (e.g., within about 30 minutes before falling asleep) and/or at other times. In some embodiments, the second RVS is delivered within about 30 minutes of an end of the sleep session (e.g., within about 30 minutes of waking up) and/or at other times. In some embodiments, control component 30 controls sensory stimulator 16 such that the first and second RVS are about 1-2 minutes in duration and comprise about 5-10 second periods of flashing light separated from each other by about 5-10 second periods of no stimulation. In some embodiments, the 5-10 second periods of no stimulation are randomized by control component 30 within the 5-10 second range. In some embodiments, the frequency of the flashing light is about 10-30 Hz. The intermittent timing is useful to counter the effects of habituation of subject 12 to the flashing light (e.g., the SSVEP response decreasing after long periods of stimulation) and/or fatigue. However, in some embodiments, control component 30 may be configured to cause sensory stimulator 16 to deliver continuous stimulation for longer periods. In these embodiments, in addition to the SSVEP response, the decline in the SSVEP response as consequence of habituation may be used to quantify the sleep need dissipation. It may be expected that the SSVEP response will habituate faster if the cortical connectivity is higher. Consequently, the stronger the sleep need dissipation is then the slower habituation will be.

In some embodiments, the RVS parameters (e.g., the 1-2 minute duration, the 5-10 second periods of flashing, the 5-10 second periods of no stimulation, the 10-30 Hz frequency) may be determined at manufacture of system 10, determined by control component 30 based on sleep need dissipation in subject 12 during previous sleep sessions, set and/or adjusted by subject 12 and/or other users via user interface 24, and/or or determined by other methods. It should be noted that the description of the RVS parameters including 30 minute periods before and after a sleep session, the 1-2 minute duration, the 5-10 second periods of flashing, the 5-10 second periods of no stimulation, and the 10-30 Hz frequency is not intended to be limiting. Control component 30 may cause sensory stimulator 16 to deliver the first and/or second RVS with any parameters that allow system 10 to function as described herein.

Parameter component 32 is configured to determine brain activity parameters in subject 12. Parameter component 32 is configured to determine the brain activity parameters based on the output signals and/or other information. In some embodiments, the one or more brain activity parameters include EEG related parameters such as power in various frequency bands of the EEG, ratios of power in a low frequency band to power in a high frequency band, and/or other parameters. In some embodiments, parameter component 32 is configured such that the one or more brain activity parameters are and/or are related to a frequency, amplitude, phase, and/or presence of specific patterns such as spindles, K-complexes, or sleep slow waves, alpha waves, and/or other characteristics of the EEG signal. In some embodiments, determining the one or more brain activity parameters includes filtering the EEG signal, additively combining and/or performing other mathematical operations on the individual oscillatory components related to brain activity, and/or other operations. For example, in some embodiments, the one or more brain activity parameters are determined based on the frequency, amplitude, and/or other characteristics of the EEG signal. In some embodiments, the determined brain activity parameters and/or the characteristics of the EEG may be and/or indicate sleep states during a past sleep session that correspond to REM and/or NREM sleep stages.

Figure 2:
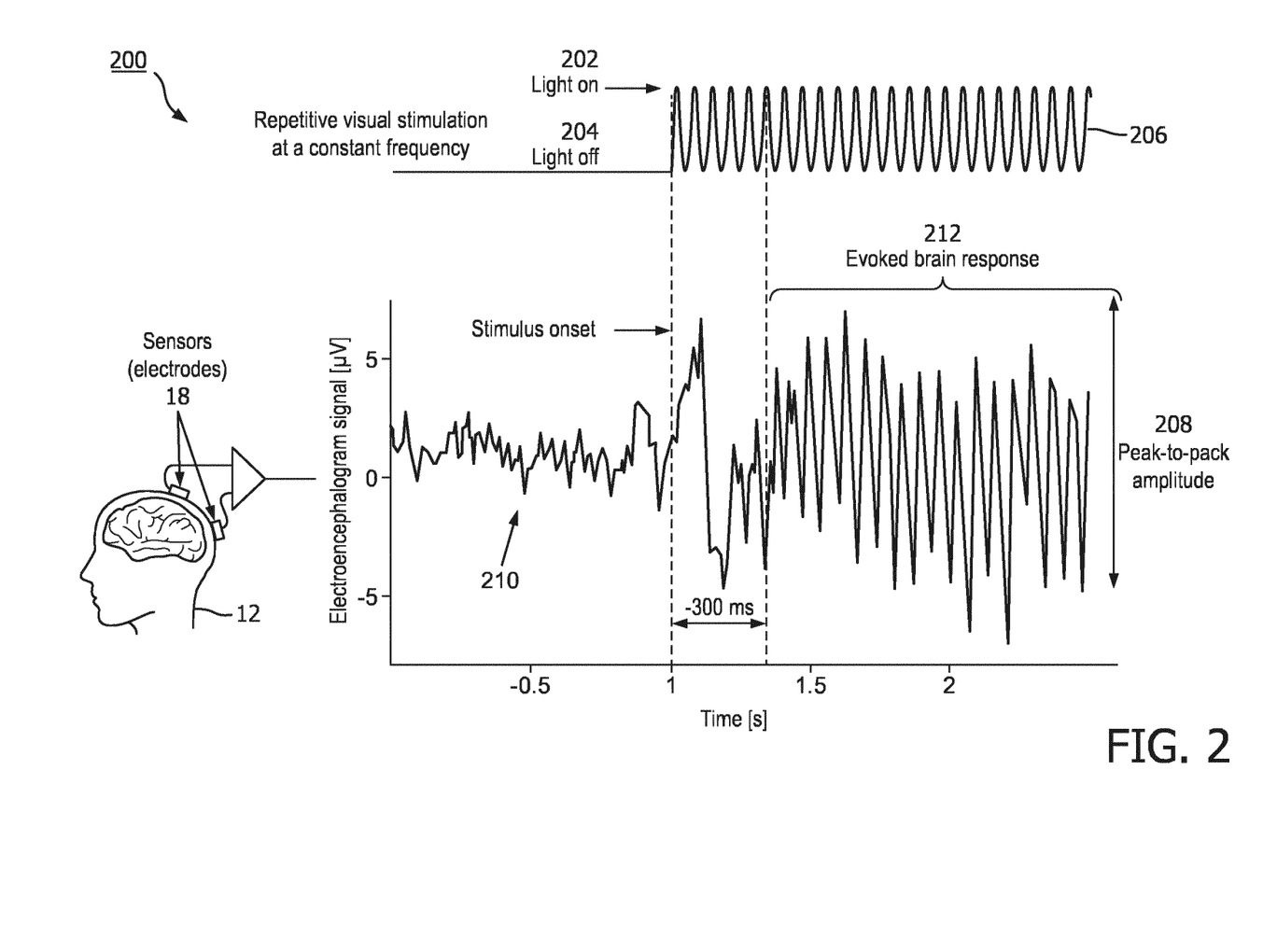
FIG. 2 illustrates an electroencephalogram (EEG) signal comprising oscillatory components at and/or about a frequency of repetitive visual stimulation provided to the subject.

In some embodiments, determining the brain activity parameters includes determining the SSVEP response of subject 12 to the RVS and/or other parameters. Parameter component 32 is configured to determine the SSVEP responses of subject 12 by determining peak to peak amplitude of the EEG signal from subject 12 evoked by the RVS, and/or other parameters. The RVS modulates the electrical activity of the brain and parameter component 32 determines the SSVEP response of subject 12 based on the EEG signal and/or other information. The EEG signal comprises oscillatory components at and/or about the frequency of the RVS and/or harmonics. This is illustrated in FIG. 2. FIG. 2 illustrates RVS 200. RVS 200 comprises on 202 and off 204 flickering light at a constant frequency 206. As shown in FIG. 2, the peak-to-peak amplitude 208 of the EEG signal 210 characterizes the response 212 of subject 12 to RVS 200. In some embodiments, the SSVEP response of subject 12 is more prominent when EEG electrodes (sensor 18) are coupled with subject 12 in occipital locations (e.g., as shown in FIG. 2).

Figure 3:
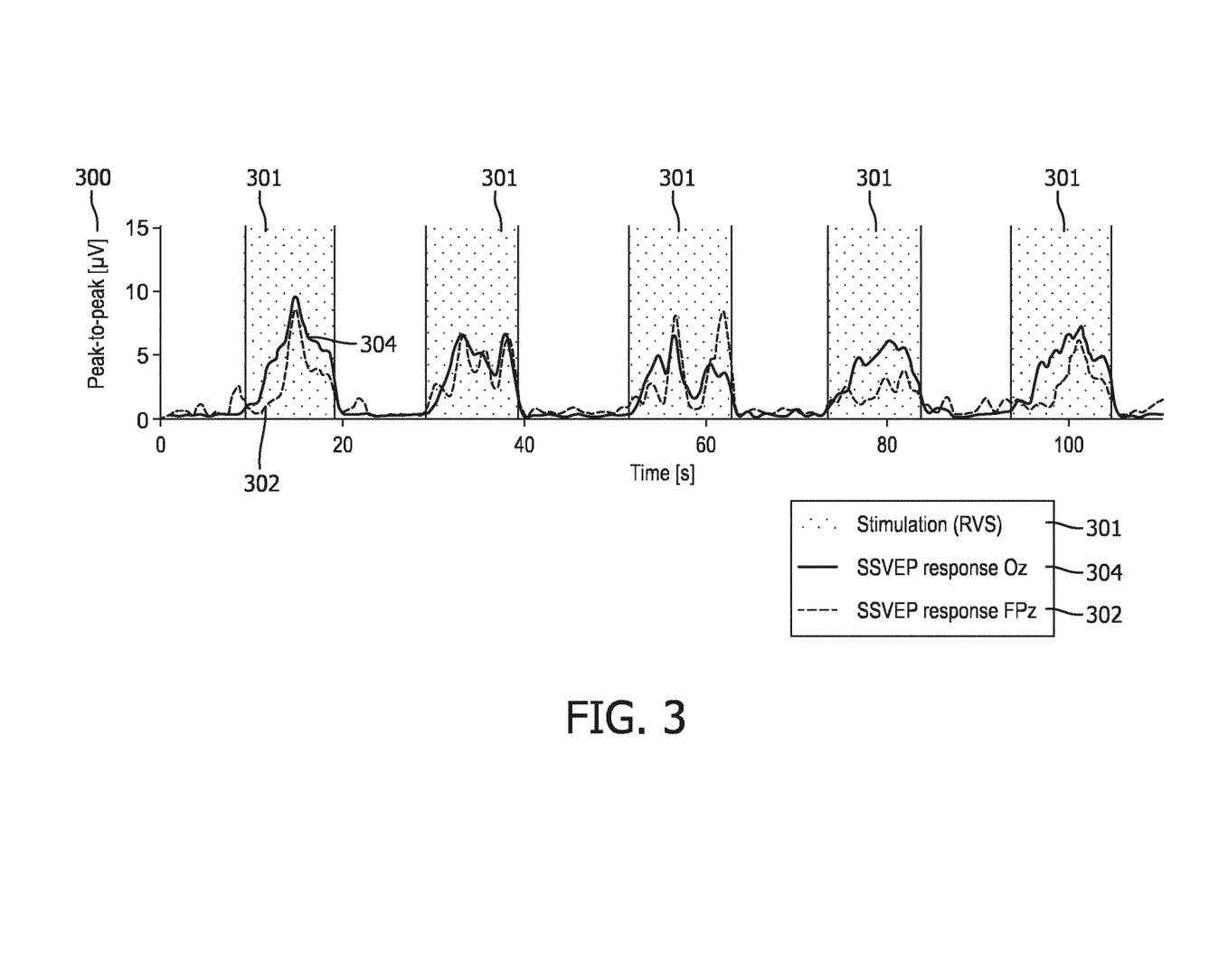
FIG. 3 illustrates steady state visually evoked potential responses of the subject when monitored with EEG electrodes coupled with the subject at occipital locations and frontal locations on the head of the subject.

As shown in FIG. 3, depending on the RVS 301 frequency, the SSVEP response (e.g., peak to peak amplitude 300) of subject 12 (FIG. 1) may be identifiable via signals (FPz) 302 from EEG electrodes coupled with subject 12 in frontal locations, though such an SSVEP response has a lower amplitude (relative to signals (Oz) 304 from EEG electrodes coupled with subject 12 in occipital locations). The amplitude of the SSVEP response depends on the RVS frequency and is higher when the RVS frequency is in the 10 to 30 Hz range (e.g., the non-limiting range described above), for example. In some embodiments, determining the SSVEP response via signals generated by EEG electrodes at occipital locations on subject 12 may be cumbersome because placement of electrodes in occipital locations typically requires the use of conductive gel (e.g., so brain activity signals are not interrupted by the hair of subject 12) and skill to position the electrodes at the right locations. Determining the SSVEP response via EEG electrodes placed at frontal locations may be more convenient for subject 12 and/or other users.

Returning to FIG. 1, parameter component 32 is configured to determine a first SSVEP response of subject 12 before the sleep session, a second SSVEP response of subject 12 after the sleep session, and/or other SSVEP responses of subject 12. Parameter component 32 is configured to determine the SSVEP responses (e.g., the first and second responses) based on the output signals from sensors 18 and/or based on other information. Parameter component 32 is configured to determine the first (e.g., before the sleep session) SSVEP response of subject 12 based on the output signals during the first RVS (e.g., the RVS delivered before the sleep session). Parameter component 32 is configured to determine the second (e.g., after the sleep session) SSVEP response of subject 12 based on the output signals during the second RVS (e.g., the RVS delivered after the sleep session).

In some embodiments, parameter component 32 is configured such that determining an individual one of the first and/or second SSVEP response comprises band pass filtering the EEG output signal during the first and/or second RVS at about a frequency of a corresponding one of the first and/or second RVS with a bandwidth of the filtering of about 1 Hz, and determining an average peak-to-peak amplitude of the EEG output signal (e.g., across RVS intervals) after filtering the EEG output signal. In some embodiments, a peak filter which also band pass filters the signal around the harmonics, is used instead of and/or in addition to the band pass filtering described above (e.g., such that the presence of harmonics in the SSVEP response are taken into account).

In some embodiments, parameter component 32 is configured to determine the first and/or second SSVEP responses of subject 12 in an ongoing manner before and/or after a sleep session, at predetermined intervals before and/or after a sleep session, and/or at other times. In some embodiments, the filtering parameters (e.g., a frequency corresponding to the RVS with a bandwidth of about 1 Hz) may be determined at manufacture of system 10, determined by parameter component 32 based on sleep need dissipation in subject 12 during previous sleep sessions, set and/or adjusted by subject 12 and/or other users via user interface 24, and/or or determined by other methods. It should be noted that the description of filtering at about a frequency corresponding to the RVS with a bandwidth of about 1 Hz is not intended to be limiting. Parameter component 32 may filter the EEG output signal with any filtering parameters that allow system 10 to function as described herein.

Comparison component 34 is configured to compare the second SSVEP response (e.g., the post sleep session SSVEP response) to the first SSVEP response (e.g., the pre sleep session SSVEP response). The brain activity response of subject 12 to the same type of stimulation (e.g., the first and second RVS) decreases after the sleep session. This decrease is dependent on the SWA during the sleep session (which is not determined but which is indicative of sleep need dissipation in subject 12 that occurs during the sleep session). Comparison component 34 is configured such that comparing the second SSVEP response to the first SSVEP response comprises determining a value of a difference between the second SSVEP response and the first SSVEP response. This difference may be determined by subtracting a value of the first SSVEP response (e.g., in μV) from a value of the second SSVEP response (e.g., in μV) and dividing the result by the value of the first SSVEP response (e.g., (after-before)/before), and/or performing other mathematical operations. In addition to the amplitude of the SSVEP, it is also possible to quantify the SSVEP response using the power (e.g., in $\mu V^2$) in a narrow band (e.g. 1-Hz wide) around the stimulation frequency. The power may also be estimated in narrow bands around the harmonic frequencies of the stimulation and these may be combined (e.g. summed).

Sleep need dissipation component 36 is configured to determine the sleep need dissipation for the sleep session based on the comparison of the second SSVEP response (e.g., the post sleep session SSVEP response) to the first SSVEP response (e.g., the pre sleep session SSVEP response). In some embodiments, sleep need dissipation component 36 is configured such that determining the sleep need dissipation for the sleep session based on the comparison comprises correlating the difference between the second SSVEP response and the first SSVEP response to a level of slow wave activity (SWA) in the subject during the sleep session. The level of SWA is indicative of the sleep need dissipation (e.g., as described above). Sleep need dissipation component 36 is configured to determine the sleep need dissipation (e.g., the sleep restoration) based on the linear relation SWA=(A×Δ SSVEP response)+B; where A and B are estimated from a linear regression model for Δ SSVEP response and SWA for subject 12 and/or a population of users demographically similar to subject 12, and/or other sources of information. The SWA is directly correlated with sleep need dissipation. In some embodiments, this number may be compared to reference values obtained from an age-matched population. Thus it may be possible to state that the level of restoration is a certain percentage of that corresponding to the age matched reference value. An example of such a linear regression model is illustrated in FIG. 4.

Figure 4:
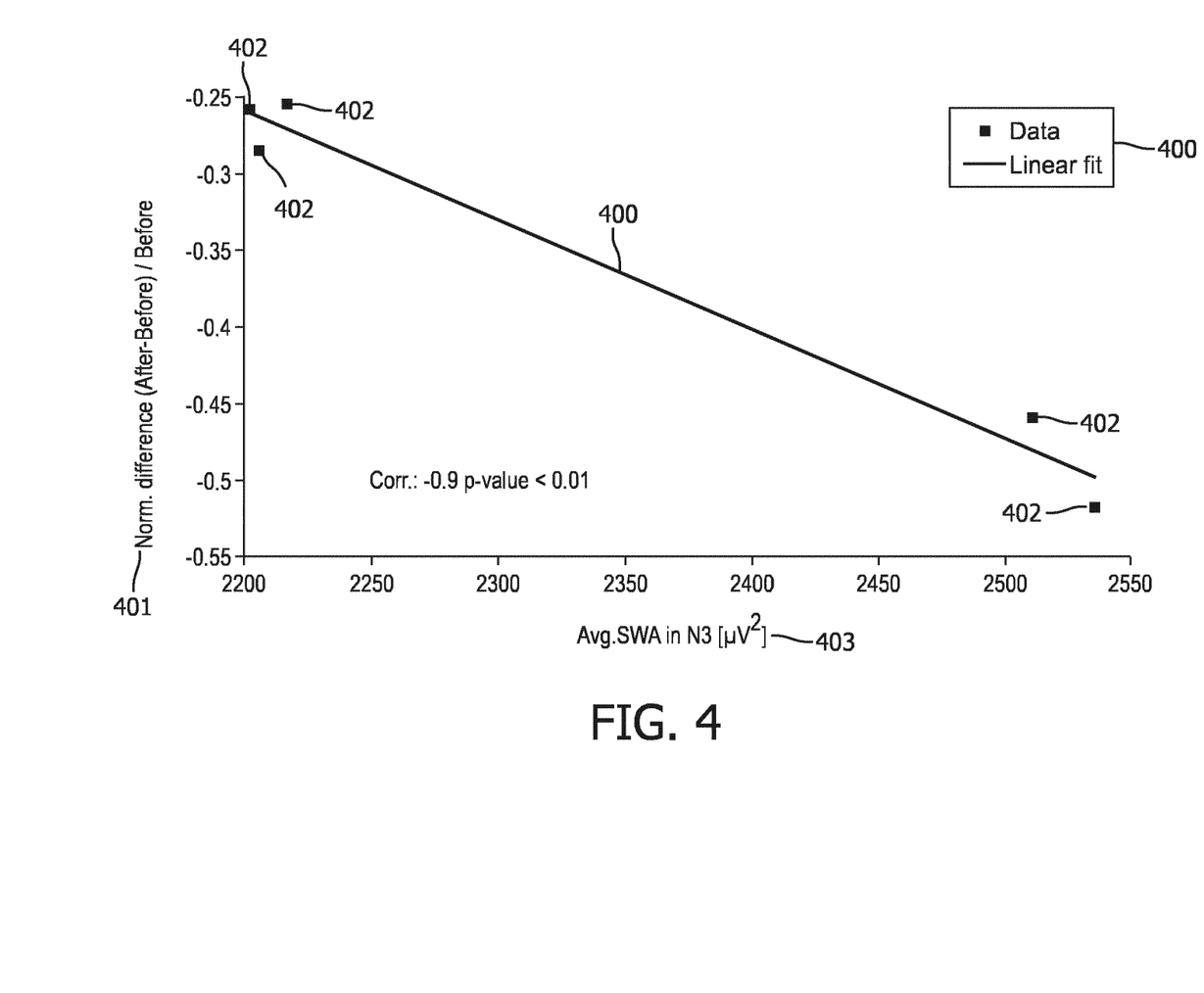
FIG. 4 illustrates a linear regression model for a change in steady state visually evoked potential responses and slow wave activity in the subject.

FIG. 4 illustrates a linear regression model 400 for the change in SSVEP responses 401 and SWA 403 for five sleep sessions 402 of a subject (e.g., subject 12). In some embodiments, model 400 and/or other similar models are predetermined before the sleep session of subject 12 (FIG. 1) described herein and stored in electronic storage 22 and/or other electronic databases. In some embodiments, model 400 and/or other similar models are determined by sleep need dissipation component 36 based on previously generated data, and/or by other computing systems. In some embodiments, model 400 and/or other similar models are programmed in system 10 at manufacture, programmed and/or adjusted by subject 12 and/or other users via user interface 24, and/or determined in other ways. Sleep need dissipation component 36 is configured to access model 400 and/or similar models when determining the sleep need dissipation as described above.

Model 400 and/or other similar models are generated by providing RVS to a subject before a sleep session, recording an EEG for the sleep session, providing RVS after the sleep session, determining SWA for the sleep session, determining the change in SSVEP response caused by the sleep session, and plotting the determined information on a chart like the one shown in FIG. 4. This process is repeated for several sleep sessions (e.g., five sleep sessions for FIG. 4), and/or for several subjects and the linear regression model is generated based on the plotted data.

To generate model 400, prior to a sleep session and after a sleep session, the subject (e.g., subject 12) received repetitive visual stimulation for three 10-second long intervals separated from each other by a 10-seocnd long break (1 minute in total) while his EEG was acquired at 250 Hz on the central occipital location Oz using BRAINQUIRY's PET EEG system. The frequency of the stimulation was 15 Hz with a 50% duty cycle. The stimulation was rendered using a 10 cm square panel which had a power LED shining green light. For individual sleep sessions, the duration of N3 sleep in minutes and the average SWA (across N3 sleep) were quantified (Table I). The SSVEP response was quantified by measuring the average peak-to-peak amplitude of the filtered EEG in the frequency band from 14.5 to 15.5 Hz (e.g., 1 Hz around the frequency of stimulation) during the periods of stimulation (Table I).

TABLE I

| Night # | N3 duration [min] | Average SWA [μV²] | Average SSVEP: peak-to-peak before sleep [μV] | Average SSVEP: peak-to-peak after sleep [μV] | Change fraction: (After-Before)/Before |
|---|---|---|---|---|---|
| 1 | 85.2 | 2510.7 | 9.65 | 5.22 | −0.46 |
| 2 | 72.2 | 2204.8 | 6.67 | 4.77 | −0.28 |
| 3 | 69.7 | 2215.9 | 6.53 | 4.87 | −0.25 |
| 4 | 72.6 | 2201.9 | 6.13 | 4.55 | −0.26 |
| 5 | 52.5 | 2535.3 | 7.25 | 3.50 | −0.52 |

The graph in FIG. 4 shows the scatter plot of the change in SSVEP response (far right column in Table I) after and before sleep, normalized by the SSVEP response before, versus the average SWA (center column in Table I). A negative correlation can be observed in FIG. 4 between the change in SSVEP response and the average SWA. In the example shown in FIG. 4, model 400 is established based on five sleep sessions for a single subject. This is not intended to be limiting. The regression model described above may be determined based on multiple sleep sessions from multiple subjects.

Figure 5:
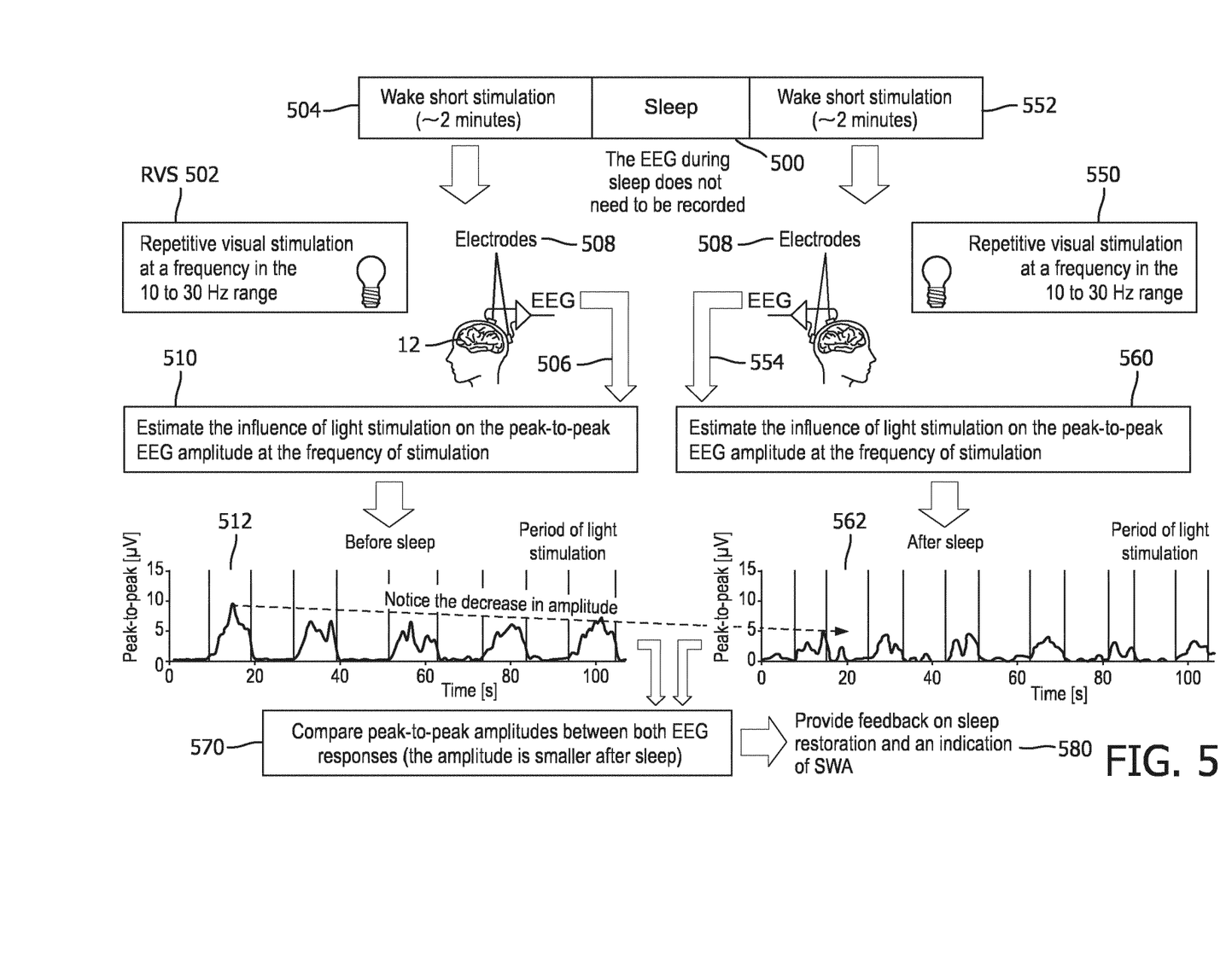
FIG. 5 summarizes the operations performed by the system.

FIG. 5 summarizes the operations performed by system 10 (FIG. 1). Before a sleep session 500, RVS 502 is provided to subject 12 (e.g., via sensory stimulator 16 controlled by control component 30 shown in FIG. 1) during a wakeful period 504. EEG output signals 506 from EEG electrodes 508 (e.g., sensors 18 shown in FIG. 1) are analyzed 510 (e.g., by comparison component 34 shown in FIG. 1) to determine a SSVEP response 512 of subject 12 to RVS 502. After sleep session 500, RVS 550 is provided to subject 12 (e.g., via sensory stimulator 16 controlled by control component 30 shown in FIG. 1) during a wakeful period 552. EEG output signals 554 from EEG electrodes 508 (e.g., sensors 18 shown in FIG. 1) are analyzed 560 (e.g., by comparison component 34 shown in FIG. 1) to determine a SSVEP response 562 of subject 12 to RVS 550. Finally, the sleep need dissipation for sleep session 500 is determined 580 (e.g., by sleep need dissipation component 36 shown in FIG. 1) based on a comparison 570 (e.g., by comparison component 34 shown in FIG. 1) of SSVEP response 562 (e.g., the post sleep session SSVEP response) to SSVEP response 512 (e.g., the pre sleep session SSVEP response) and/or other information as described herein.

Returning to FIG. 1, in some embodiments, components 30, 32, 34, and/or 36 are configured such that, responsive to sleep patterns for subject 12 being sufficiently regular, the first SSVEP response (e.g., before sleep) need not be determined. In some embodiments, system 10 is configured such that a subject is considered regular if her/his bedtime and wake-up time are both within an hour range for 80% of the nights (e.g., sleep sessions). Instead, the first SSVEP response (e.g., before sleep) is set to a default value (e.g., the average of values in the center column of Table I). This embodiment may be advantageous because determining the SSVEP response only once (e.g., in the morning after waking up) after a sleep session is required.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver, subject 12, and/or other users via user interface 24. As another example, user interface 24 may be and/or be included in a computing device comprising a display screen that forms sensory stimulator 16 such that the RVS is delivered to subject 12 via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 6:
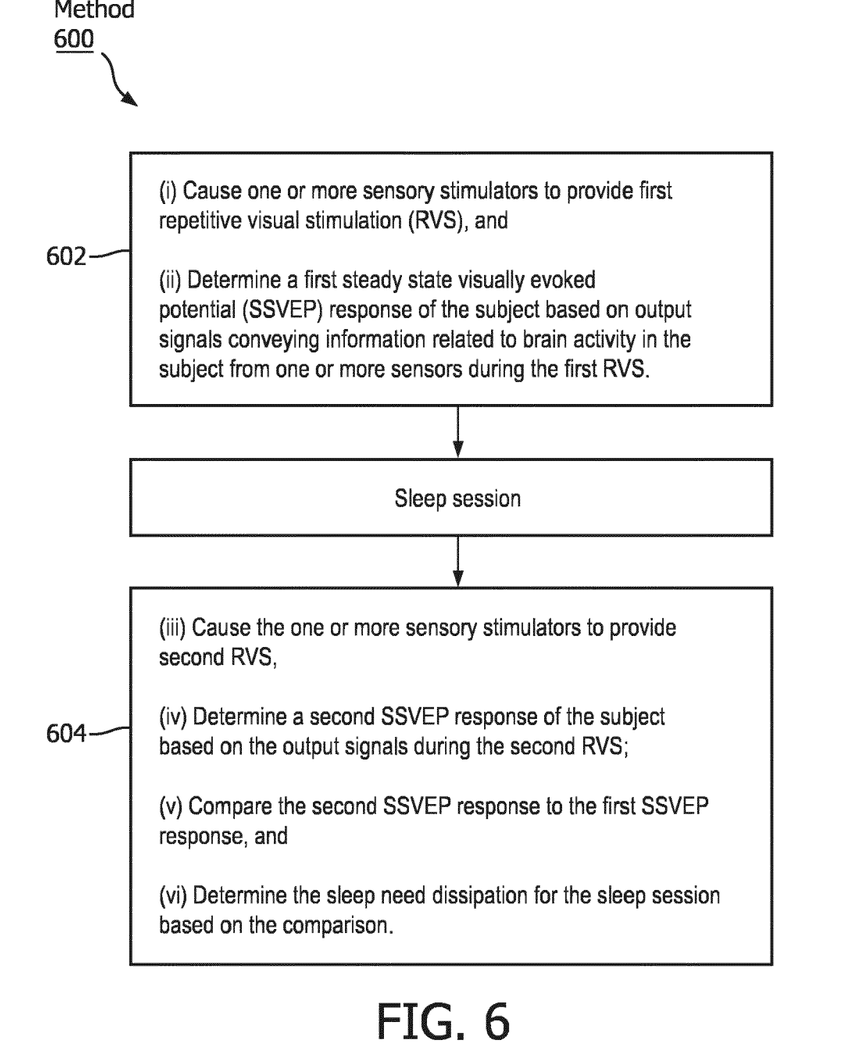
FIG. 6 illustrates a method for determining sleep need dissipation in a subject without monitoring brain activity during a sleep session.

FIG. 6 illustrates a method 600 for determining sleep need dissipation in a subject without monitoring brain activity during a sleep session. Method 600 is performed with a determination system comprising one or more sensory stimulators, one or more sensors, one or more hardware processors, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, before the sleep session, (i) the one or more sensory stimulators are caused to provide first repetitive visual stimulation (RVS), and (ii) a first steady state visually evoked potential (SSVEP) response of the subject is determined based on output signals conveying information related to brain activity in the subject from the one or more sensors during the first RVS. In some embodiments, operation 602 is performed by a hardware processor the same as or similar to processor 20 (shown in FIG. 1 and described herein).

At an operation 604, after the sleep session, (iii) the one or more sensory stimulators are caused to provide second RVS, (iv) a second SSVEP response of the subject is determined based on the output signals during the second RVS; (v) the second SSVEP response is compared to the first SSVEP response, and (vi) the sleep need dissipation for the sleep session is determined based on the comparison. In some embodiments, determining the sleep need dissipation for the sleep session based on the comparison comprises correlating a difference between the second SSVEP response and the first SSVEP response to a level of slow wave activity (SWA) in the subject during the sleep session. The level of SWA is indicative of the sleep need dissipation.

In some embodiments, the one or more sensors comprise electroencephalogram (EEG) electrodes, which are coupled with the subject before and after the sleep session, but not during the sleep session. In some embodiments, the EEG electrodes are configured to be coupled at occipital locations or frontal locations on a head of the subject before and after the sleep session. In some embodiments, determining an individual one of the first and/or second SSVEP response comprises: band pass filtering an EEG output signal during the first and/or second RVS at about a frequency of a corresponding one of the first and/or second RVS with a bandwidth of the filtering of about 1 Hz; and determining an average peak-to-peak amplitude of the EEG output signal after filtering the EEG output signal. In some embodiments, the one or more sensory stimulators comprise a display screen of a computing device or a lighting panel, wherein the first and second RVS are about 1-2 minutes in duration and comprise about 5-10 second periods of flashing light separated from each other by about 5-10 second periods of no stimulation, and wherein a frequency of the flashing light is about 10-30 Hz.

In some embodiments, operation 604 is performed by a hardware processor the same as or similar to processor 20 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine sleep need dissipation in a subject without monitoring brain activity during a sleep session, the system comprising:
    one or more sensory stimulators configured to provide repetitive visual stimulation (RVS) to the subject;
    one or more sensors configured to generate output signals conveying information related to brain activity in the subject; and
    one or more hardware processors operatively communicating with the one or more sensory stimulators and the one or more sensors, the one or more hardware processors configured by machine-readable instructions to:
        before the sleep session, (i) cause the one or more sensory stimulators to provide first RVS, and (ii) determine a first steady state visually evoked potential (SSVEP) response of the subject based on the output signals during the first RVS; and
        after the sleep session, (iii) cause the one or more sensory stimulators to provide second RVS, (iv) determine a second SSVEP response of the subject based on the output signals during the second RVS; (v) compare the second SSVEP response to the first SSVEP response, and (vi) determine the sleep need dissipation for the sleep session based on the comparison, wherein determining the sleep need dissipation for the sleep session based on the comparison comprises correlating a difference between the second SSVEP response and the first SSVEP response to a level of slow wave activity (SWA) in the subject during the sleep session, the level of SWA being indicative of the sleep need dissipation.

2. The system of claim 1, wherein the one or more sensors comprise electroencephalogram (EEG) electrodes.

3. The system of claim 2, wherein the one or more hardware processors are configured such that determining an individual one of the first and/or second SSVEP response comprises:
    band pass filtering an EEG output signal during the first and/or second RVS at about a frequency of a corresponding one of the first and/or second RVS with a bandwidth of the filtering of about 1 Hz; and
    determining an average peak-to-peak amplitude of the EEG output signal after filtering the EEG output signal.

4. The system of claim 2, wherein the EEG electrodes are configured to be coupled at occipital locations or frontal locations on a head of the subject before and after the sleep session.

5. The system of claim 1, wherein the one or more sensory stimulators comprise a display screen of a computing device or a lighting panel, wherein the first and second RVS are about 1-2 minutes in duration and comprise about 5-10 second periods of flashing light separated from each other by about 5-10 second periods of no stimulation, and wherein a frequency of the flashing light is about 10-30 Hz.

6. A method for determining sleep need dissipation in a subject without monitoring brain activity during a sleep session, the method performed by a determination system comprising one or more sensory stimulators, one or more sensors, and one or more hardware processors, the method comprising:
    before the sleep session, with the one or more hardware processors, (i) causing the one or more sensory stimulators to provide first repetitive visual stimulation (RVS), and (ii) determining a first steady state visually evoked potential (SSVEP) response of the subject based on output signals conveying information related to brain activity in the subject from the one or more sensors during the first RVS; and
    after the sleep session, with the one or more hardware processors, (iii) causing the one or more sensory stimulators to provide second RVS, (iv) determining a second SSVEP response of the subject based on the output signals during the second RVS; (v) comparing the second SSVEP response to the first SSVEP response, and (vi) determining the sleep need dissipation for the sleep session based on the comparison, wherein determining the sleep need dissipation for the sleep session based on the comparison comprises correlating a difference between the second SSVEP response and the first SSVEP response to a level of slow wave activity (SWA) in the subject during the sleep session, the level of SWA being indicative of the sleep need dissipation.

7. The method of claim 6, wherein the one or more sensors comprise electroencephalogram (EEG) electrodes, and wherein the method further comprises coupling the EEG electrodes with the subject before and after the sleep session, but not during the sleep session.

8. The method of claim 7, wherein determining an individual one of the first and/or second SSVEP response comprises:
    band pass filtering an EEG output signal during the first and/or second RVS at about a frequency of a corresponding one of the first and/or second RVS with a bandwidth of the filtering of about 1 Hz; and
    determining an average peak-to-peak amplitude of the EEG output signal after filtering the EEG output signal.

9. The method of claim 7, wherein the EEG electrodes are configured to be coupled at occipital locations or frontal locations on a head of the subject before and after the sleep session.

10. The method of claim 6, wherein the one or more sensory stimulators comprise a display screen of a computing device or a lighting panel, wherein the first and second RVS are about 1-2 minutes in duration and comprise about 5-10 second periods of flashing light separated from each other by about 5-10 second periods of no stimulation, and wherein a frequency of the flashing light is about 10-30 Hz.

11. A system configured to determine sleep need dissipation in a subject without monitoring brain activity during a sleep session, the system comprising:
    means for providing repetitive visual stimulation (RVS) to the subject;
    means for generating output signals conveying information related to brain activity in the subject; and
    before the sleep session, means for (i) causing the means for providing to provide first RVS, and (ii) determining a first steady state visually evoked potential (SSVEP) response of the subject based on the output signals during the first RVS; and
    after the sleep session, means for (iii) causing the one or more sensory stimulators to provide second RVS, (iv) determining a second SSVEP response of the subject based on the output signals during the second RVS; (v) comparing the second SSVEP response to the first SSVEP response, and (vi) determining the sleep need dissipation for the sleep session based on the comparison, wherein determining the sleep need dissipation for the sleep session based on the comparison comprises correlating a difference between the second SSVEP response and the first SSVEP response to a level of slow wave activity (SWA) in the subject during the sleep session, the level of SWA being indicative of the sleep need dissipation.

12. The system of claim 11, wherein the means for generating output signals comprise electroencephalogram (EEG) electrodes.

13. The system of claim 12, wherein determining an individual one of the first and/or second SSVEP response comprises:
  band pass filtering an EEG output signal during the first and/or second RVS at about a frequency of a corresponding one of the first and/or second RVS with a bandwidth of the filtering of about 1 Hz; and
  determining an average peak-to-peak amplitude of the EEG output signal after filtering the EEG output signal.

14. The system of claim 12, wherein the EEG electrodes are configured to be coupled at occipital locations or frontal locations on a head of the subject before and after the sleep session.

15. The system of claim 11, wherein the one or more sensory stimulators comprise a display screen of a computing device or a lighting panel, wherein the first and second RVS are about 1-2 minutes in duration and comprise about 5-10 second periods of flashing light separated from each other by about 5-10 second periods of no stimulation, and wherein a frequency of the flashing light is about 10-30 Hz.

* * * * *